(12) United States Patent
Albrecht et al.

(10) Patent No.: US 8,147,502 B2
(45) Date of Patent: Apr. 3, 2012

(54) GASTRIC COIL MANIPULATOR

(75) Inventors: Thomas E. Albrecht, Cincinnati, OH (US); Mark S. Ortiz, Milford, OH (US); Jason L. Harris, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 597 days.

(21) Appl. No.: 12/113,677

(22) Filed: May 1, 2008

(65) Prior Publication Data
US 2009/0275975 A1 Nov. 5, 2009

(51) Int. Cl.
*A61B 17/42* (2006.01)
(52) U.S. Cl. ....................................... 606/119
(58) Field of Classification Search .......... 600/201–207, 600/185–188, 374, 380; 606/119, 191, 197, 606/113; 128/898; 607/124, 125
See application file for complete search history.

(56) References Cited

U.S. PATENT DOCUMENTS

| | | | |
|---|---|---|---|
| 5,170,803 A * | 12/1992 | Hewson et al. | 607/124 |
| 6,013,024 A | 1/2000 | Mitsuda et al. | |
| 6,126,649 A | 10/2000 | Vantassel et al. | |
| 6,558,400 B2 | 5/2003 | Deem et al. | |
| 2004/0181242 A1 | 9/2004 | Stack et al. | |
| 2006/0106288 A1 | 5/2006 | Roth et al. | |
| 2006/0122462 A1 * | 6/2006 | Roth et al. | 600/204 |

FOREIGN PATENT DOCUMENTS

| | | |
|---|---|---|
| DE | 2800362 | 7/1978 |
| EP | 1852082 | 11/2007 |
| WO | WO 2008/028108 | 3/2008 |

* cited by examiner

*Primary Examiner* — Kevin T Truong
(74) *Attorney, Agent, or Firm* — Welsh Flaxman + Gitler LLC

(57) ABSTRACT

A gastric coil manipulator includes a longitudinally extending shaft having a distal end and a proximal end and a flexible element with a portion thereof extending beyond the distal end of the shaft for the creation of a resilient arc, wherein an actuator cable is secured to the flexible element for manipulation of the portion of the flexible element extending beyond the distal end of the shaft.

11 Claims, 4 Drawing Sheets

GASTRIC COIL MANIPULATOR

BACKGROUND OF THE INVENTION

1. Field of the Invention

The invention relates to bariatric surgery. More particularly, the invention relates to a medical instrument and associated procedure for manipulation of the gastric cavity to enhance the treatment thereof.

2. Description of the Related Art

During advanced endoscopic procedures, such as, endoscopic gastric restriction for obesity it is oftentimes necessary to secure anterior and posterior stomach walls in an effort to reduce stomach volume. More particularly, endolumenal vertical gastric restriction requires fastening of the internal walls (mucosal surface) of the stomach. This is true for purely endoscopic or hybrid (that is, laparoscopic/endoscopic) features. For the purposes of the present disclosure, the term endoscopic is intended to refer to procedures where access to the body is achieved via a natural body orifice for example, transorally, while the term laparoscopic is intended to refer to procedures where access to the body is achieved via a surgically created incision, for example, through the use of a trocar. The key requirements of these procedures are entry to the site, visualization of the site, orientation of the medical instrument and verification of proper location for restriction.

In practice, one must repeatably acquire the correct zone of tissue on the anterior and posterior walls of the stomach. The gastric restriction procedure requires durability of the restricted gastric cavity, which may only be achieved if the mucosal surfaces to be joined are injured, preferably excised such that the body's healing mechanism steps in and heals opposed mucosal surfaces together. The gastric restriction procedure also requires the ability to extract injured tissue (through debridement or tissue removal) from the site as may or may not be mandatory and the ability to accurately join injured zones precisely such that they line up along the anterior and posterior aspect. The gastric restriction procedure also requires the ability to appose mucosa on both sides of the anterior and posterior junction line to seal off the injured area and enhance sealing, as well as the ability to fasten opposing walls together to form a restriction.

To accomplish these goals via natural orifice access only, all devices must flex appropriately and be sized for insertion down the esophagus, which imposes a roughly 16 mm diameter size limitation and a 40-50 mm rigid length segment limitation in order to pass the flexure of the pharynx. In addition, all mechanisms must be actuated through a flexible shaft. This is a difficult task. There is also a great deal of doubt as to whether surgeons will switch from laparoscopic procedures, which are already minimally invasive and which are already being used throughout the industry, to endoscopic procedures with their steep learning curve and high difficulty of use for the benefits of a few less scars. There is, therefore, a need for an approach of performing gastric restriction that allows greater flexibility of usability, design, and robustness that can be achieved via an endoscopic approach only.

As such, a need exists for endoscopic and/or laparoscopic medical instruments and procedures overcoming these shortcomings in the currently existing technology. The present invention provides such a medical instrument and procedure.

SUMMARY OF THE INVENTION

It is, therefore, an object of the present invention to provide a manipulator including a longitudinally extending shaft having distal and proximal ends and a flexible element with a portion thereof extending beyond the distal end of the shaft for the creation of a resilient arc. The gastric coil manipulator also includes an actuator cable is secured to the flexible element for manipulation of the portion of the flexible element extending beyond the distal end of the shaft.

It is also an object of the present invention to provide a manipulator wherein the shaft is a flexible tubular member.

It is another object of the present invention to provide a manipulator wherein the flexible element is secured to the shaft in a manner allowing for longitudinal movement of the flexible element relative to the shaft.

It is a further object of the present invention to provide a manipulator wherein the flexible element includes a first end that is connected to and extends along the length of the shaft and a free second end that extends beyond the distal end. The actuator cable is secured to the flexible element adjacent the second end of the flexible element for manipulation of the portion of the flexible element extending beyond the distal end of the shaft.

It is also an object of the present invention to provide a manipulator wherein the actuator cable includes a second end which is secured to the second end of the flexible element and a first end which is accessible adjacent the proximal end of the shaft for actuation of the flexible element.

It is another object of the present invention to provide a manipulator wherein the actuator cable extends up through a cable support tube mounted adjacent the shaft.

It is a further object of the present invention to provide a manipulator wherein the cable support tube is secured to the shaft such that longitudinal axes of the respective cable support tube and the shaft are substantially parallel.

It is also an object of the present invention to provide a manipulator wherein the cable support tube is mounted upon the shaft such that the cable support tube may be moved longitudinally relative to the shaft for adjustment of the force vector which the actuator cable applies to the flexible element so as to alter a shape of the flexible element.

It is another object of the present invention to provide a manipulator including a handle at the proximal end of the shaft, wherein the handle is further provided with a lever secured to the cable support tube for manipulating the position of the cable support tube relative to the shaft.

It is a further object of the present invention to provide a manipulator including a handle at the proximal end of the shaft.

It is also an object of the present invention to provide a method for stomach manipulation. The method includes inserting a medical instrument within the gastric cavity, and splaying the gastric cavity in a manner eliminating stomach folds, ensuring proper alignment of medical instrument and ensuring proper volume of a resultant gastric pouch.

Other objects and advantages of the present invention will become apparent from the following detailed description when viewed in conjunction with the accompanying drawings, which set forth certain embodiments of the invention.

DESCRIPTION OF THE PREFERRED EMBODIMENT

Figure 1:
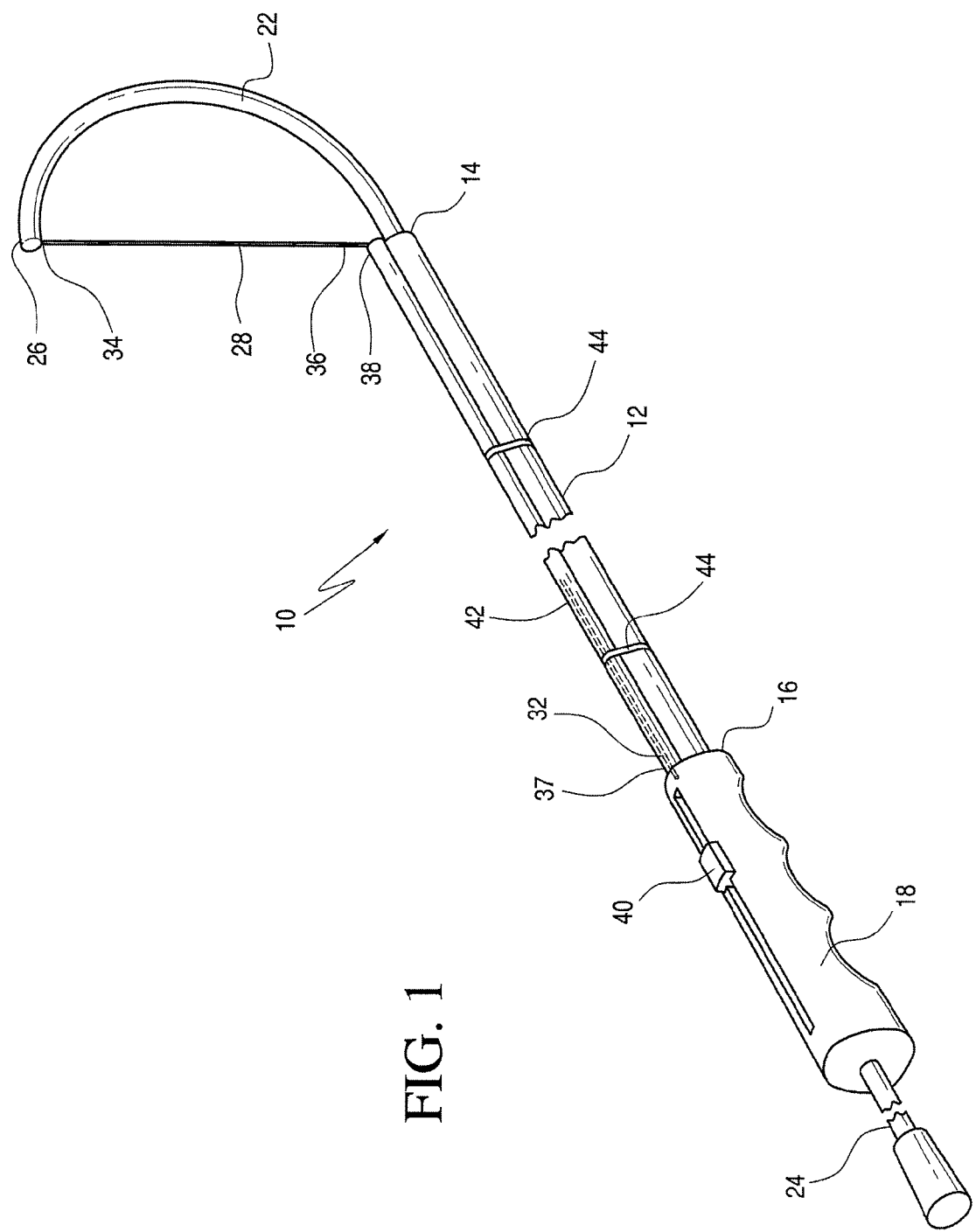
FIG. 1 is a medical instrument in accordance with a preferred embodiment of the present invention.
Figure 2:
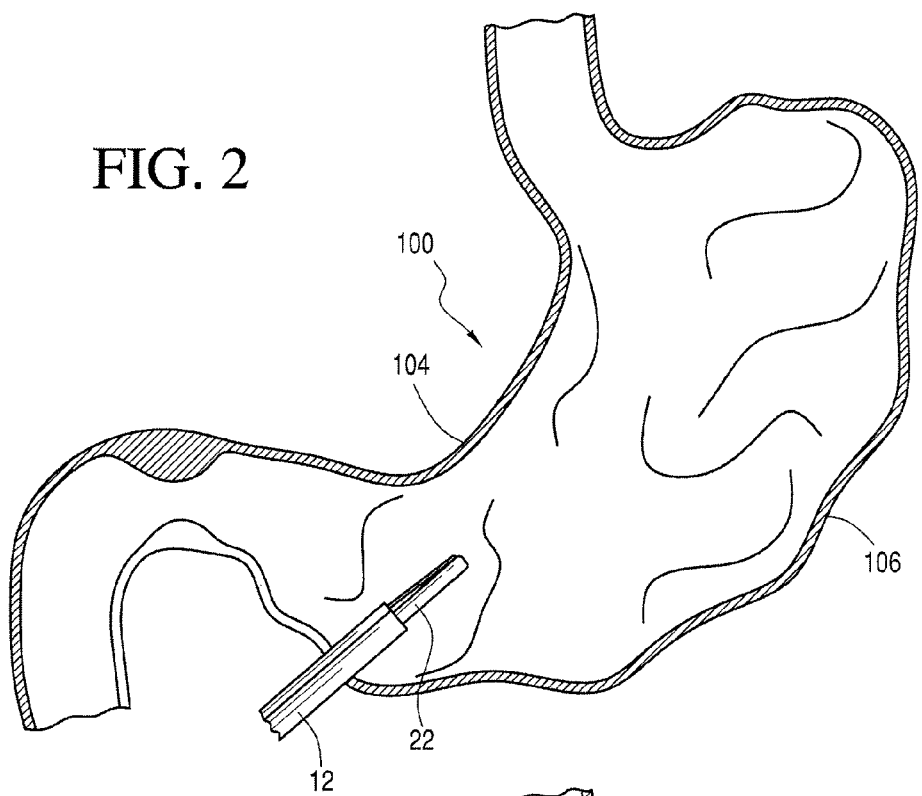
FIGS. 2, 3, 4, 5 and 6 show the steps associated with usage of the present medical instrument.
Figure 3:
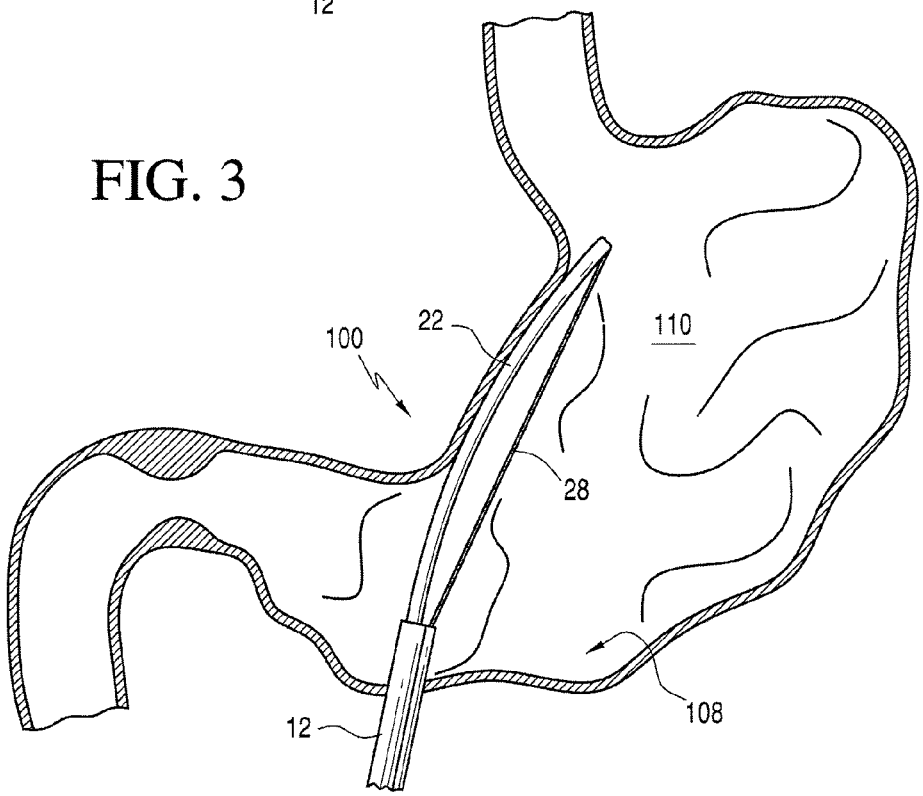
Figure 4:
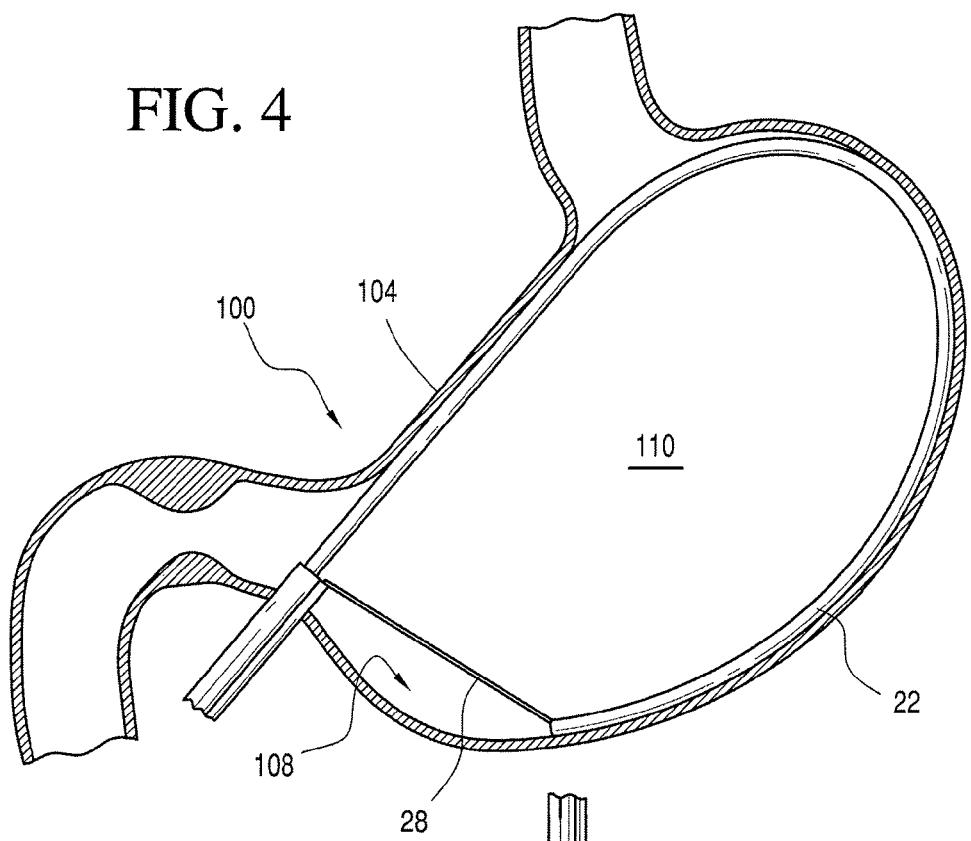
Figure 5:
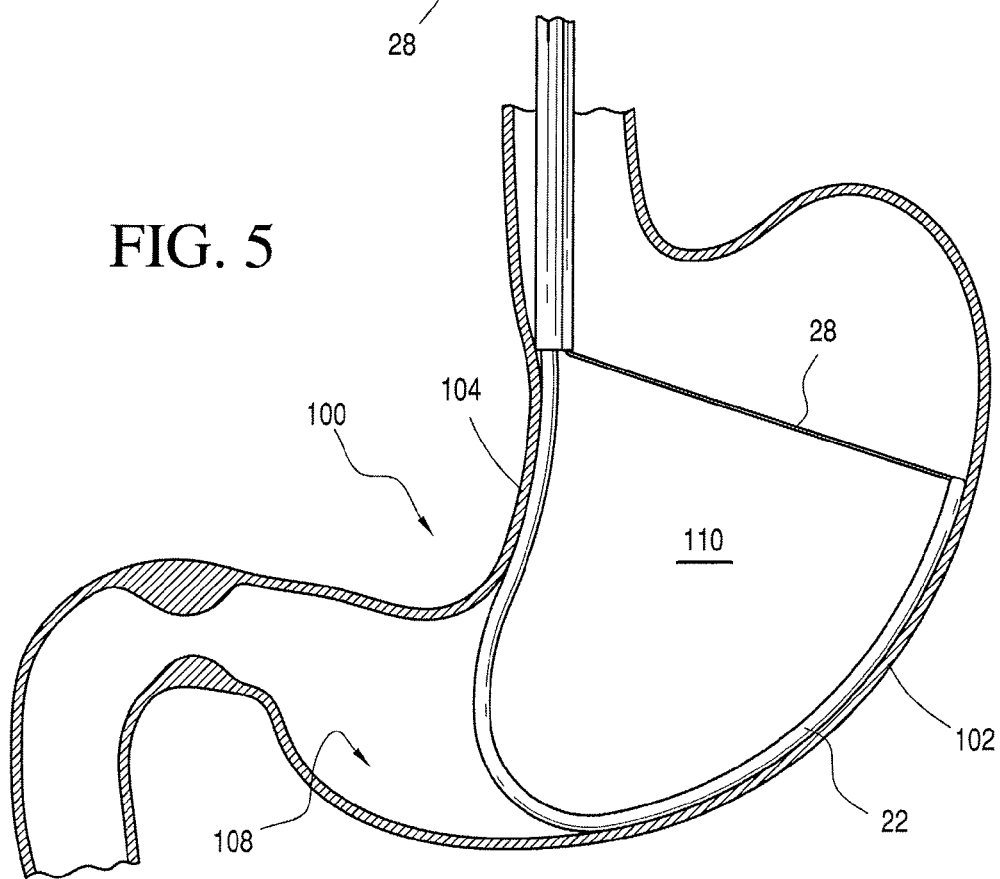
Figure 6:
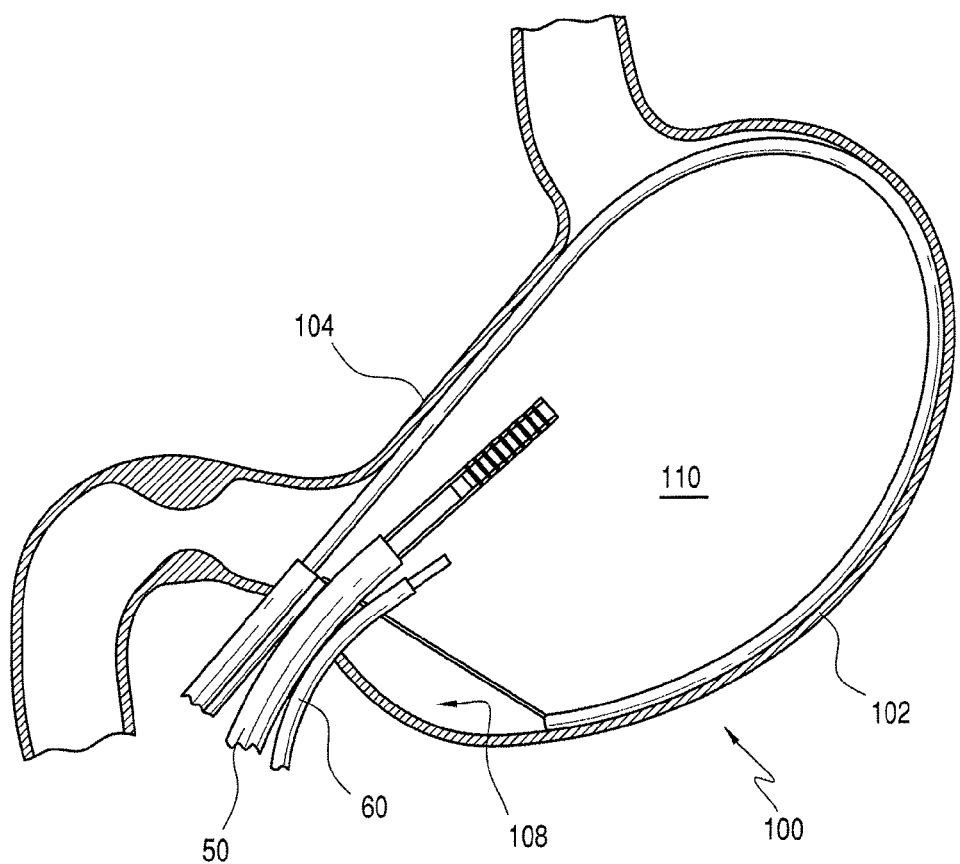

The detailed embodiment of the present invention is disclosed herein. It should be understood, however, that the disclosed embodiment is merely exemplary of the invention, which may be embodied in various forms. Therefore, the details disclosed herein are not to be interpreted as limiting, but merely as a basis for teaching one skilled in the art how to make and/or use the invention.

With reference to the various figures, an endoscopic and/or laparoscopic medical instrument for stomach stabilization in the form of a gastric coil manipulator (more generally, a lumen manipulator) 10 is disclosed. As will be discussed below in greater detail, the gastric coil manipulator 10 is an elongated, flexible medical instrument designed to allow for controlled manipulation, in particular, spreading, of the walls 102 of the stomach 100. The gastric coil manipulator 10 is easily introduced endoscopically and provides a framework for holding the stomach tissue during insufflation and/or application of vacuum for subsequent work on the tissue of the stomach. The gastric coil manipulator 10 also provides a reference point for manipulating medical instruments to their desired locations in a predictable manner. In accordance with a preferred embodiment, it is contemplated the present gastric coil manipulator 10 is well suited for use in conjunction with the device and method disclosed in commonly owned U.S. Patent Application Publication No. 2007/0276409, entitled "ENDOSCOPIC GASTRIC RESTRICTION METHODS AND DEVICES", which is incorporated herein by reference. While the present manipulator is disclosed for preferred use in the gastric cavity, it is contemplated it may be used in various other applications without departing from the spirit of the present invention.

The present gastric coil manipulator 10 accomplishes stomach manipulation to eliminate stomach folds, ensure proper alignment of medical instruments with the lesser curve 104 of the stomach 100 and ensure proper volume of a resultant gastric pouch. That is, where a medical practitioner is attempting to work relative to the lesser curve 104 of the stomach 100, for example, while laying down a gastroplasty, the present gastric coil manipulator 10 helps spread and control the stomach in a manner ensuring the gastroplasty is performed in a uniform manner, and not variable because of stomach folds or rugae, that is, the walls 102 of the stomach are now smooth throughout the its length as a result of the spreading provided by the present gastric coil manipulator. Stomach spreading and approximation is accomplished by using the present gastric coil manipulator 10 as disclosed with reference to FIG. 1, which may enter the stomach through a laparoscopic incision or endoscopically in a transoral manner.

More particularly, the gastric coil manipulator 10 includes a longitudinally extending shaft 12 having a distal end 14 and a proximal end 16. The shaft 12 is preferably a flexible tubular member adapted for the passage of various endoscopic instruments therethrough. The proximal end 16 includes a handle 18 for engagement by the medical practitioner using the gastric coil manipulator 10.

The gastric coil manipulator 10 further includes a flexible element 22 which extends longitudinally within the shaft 12 and a portion thereof extends beyond the distal end 14 of the shaft 12 for the creation of a resilient arc used in the manipulation of the stomach in a manner discussed below in detail. More particularly, the flexible element 22 is secured to the shaft 12 in a manner allowing for longitudinal movement of the flexible element 22 relative to the shaft 12. Because the flexible element 22 is capable of being moved relative to the shaft 12, users of the present gastric coil manipulator 10 may adjust the length of that portion of the flexible element 22 that extends beyond the distal end 14 of the shaft 12.

The flexible element 22 includes a first end 24 that is connected to and extends along the length of the shaft 12 and a free second end 26 that extends beyond the distal end 14 of the shaft 12. An actuator cable 28 is secured to the flexible element 22 adjacent the free second end 26 of the flexible element 22 for manipulation of the portion of the flexible element 22 extending beyond the distal end 14 of the shaft 12. The actuator cable 28 includes a second end 34 which is secured to the free second end 26 of the flexible element 22 as discussed above and a first end 32 which is accessible adjacent the proximal end 16 of the shaft 12 for actuation of the flexible element 22. The central portion 36 of the actuator cable 28 is located between the first end 32 and the second end 34 thereof and extends up through a cable support tube 42 mounted adjacent the shaft 12.

More particularly, the cable support tube 42 includes a proximal end 37 and a distal end 38. The cable support tube 42 is secured to the shaft 12 such that the longitudinal axes of the respective cable support tube 42 and the shaft 12 are substantially parallel when both are straight as shown in FIG. 1. In addition, and for reasons discussed below in greater detail, the cable support tube 42 is mounted upon the shaft 12 such that the cable support tube 42 may be moved longitudinally relative to the shaft 12 for adjustment of the force vector which the actuator cable 28 applies to the second end 26 of the flexible element 22. In accordance with a preferred embodiment, the cable support tube 42 is secured to the shaft 12 by wrap members 44 holding the cable support tube 42 adjacent the shaft 12, but allowing relative movement along the longitudinal axis of the cable support tube 42. The handle 18 is provided with a lever 40 secured to the cable support tube 42 for manipulating the position of the cable support tube 42 relative to the shaft 12.

In practice, the flexible element 22 is bent as a result of the force applied by the actuator cable 28 which exits the distal end 38 of the cable support tube 42 of the present gastric coil manipulator 10 at or near the point where the flexible element 22 is exits the distal end 14 of shaft 12. With the second end 34 of the actuator cable 28 secured to the second end 26 of the flexible element 22, and the first end 32 of the actuator cable 28 fixedly secured at the handle 18, a portion of the central portion 36 of the actuator cable rigidly extends between the second end 26 of the flexible element 22 and the distal end 38 of the cable support tube 42 tensioning the flexible element 22 into the shape of an arc.

The diameter of the arc of the flexible element 22 of the present gastric coil manipulator 10 is determined by the amount of flexible element 22 fed out of, or extending beyond, the distal end 14 of the shaft 12 and the amount of the actuator cable 28 that is retracted into the cable support tube 42 so as to pull the free second end 26 of the flexible element 22 toward the distal end 14 of the shaft 12 and the distal end 38 of the cable support tube 42. In accordance with a preferred embodiment, the length of the flexible element 22 fed out is controlled by pushing or pulling on the first end 24 of the flexible element 22 to extend or retract the second end 26 of the flexible element 22. This two-phase adjustment mechanism is further enhanced by providing for an adjustable exit point (that is, the distal end 38 of the cable support tube 42) for the actuator cable 28. This is achieved by supporting the actuator cable 28 within the cable support tube 42. As discussed above, the cable support tube 42 is secured to the shaft 12 and the flexible element 22 for movement relative thereto such that the exit point of the actuator cable 28 from the cable support tube 42 relative to the second end 26 of the flexible element 22 is easily adjusted by sliding the cable support tube 42 along the shaft 12 such that the actuator cable 28 extends beyond the distal end 38 of the cable support tube 42 (that is, the exit port) at a position that varies relative to the second end 26 of the flexible element 22 and the distal end 14 of the shaft 12.

Referring to FIGS. 2 to 6, when the gastric coil manipulator 10 is deployed in the stomach 100, the gastric coil manipulator 10 splays the stomach 100 open by outwardly pressing on the greater curve 106 and lesser curve 104. As a result of this outward force, the folds of the stomach 100 are smoothed out and the posterior wall 108 and anterior wall 110 of the stomach 100 are approximated; that is, bringing the posterior 108 and anterior wall 110 of the stomach 100 together for fixing the tissue of the anterior and posterior walls 110, 108. This tissue apposition can be used to configure the stomach 100 so that the anterior and posterior walls 110, 108 may be pulled together and permanently fixed together.

The present invention further relates to how the present gastric coil manipulator 10 may be used to control the stomach 100. Introducing the present gastric coil manipulator 10 is accomplished in accordance with the present invention as described above and may be achieved via either endoscopic and/or laparoscopic procedures. Once the stomach 100 is manipulated in accordance with the present invention, the application of multiple S-clips (as disclosed in commonly owned PCT Publication No. WO 2006/037399, entitled "Surgical Hook-Shaped Staple", which is incorporated herein by reference) enables anterior to posterior wall fixation at numerous points. These S-clips can be applied to reconfigure the stomach into multiple shapes. In accordance with a preferred procedure, the S-clips are used to create an inlet restriction within the stomach.

In accordance with an alternate embodiment, it is contemplated once the gastric coil manipulator is properly positioned within the stomach with the anterior and posterior walls drawn in apposition, the distal end of the gastric coil manipulator, that is, the flexible element may be detached from the shaft or the gastric coil manipulator may be left in place within the stomach to allow for the passage of an applicator for the S-clips, for example, within the stomach.

If the passageway provided by the lumen of the shaft 12 of the gastric coil manipulator 10 is large enough relative the flexible element 22, it may also serve as a trocar introducer sleeve for visualization, liquid, suction, therapeutic drugs or other devices. In addition, drop off visualization devices, such as are being worked on, may be attached to the present gastric coil manipulator 10 for additional imaging within the stomach. The present gastric coil manipulator 10 may also be adapted to function as a mounting platform or guide track for other devices such as a pyloric plug, an endoscope or a fastener applier device.

The present gastric coil manipulator 10 allows for stomach wall control, hybrid access, endolumenal access, stomach manipulation and rugae handling, pyloric plugging, work in conjunction with other apparatuses, devices, endoscopes 50, on board visualization 60 and may also serve as a trocar, introducer sleeve for visualization, liquid, suction, therapeutic drugs or other devices. The present invention also provides for stomach manipulation, elimination of stomach folds, proper alignment of the anterior wall and posterior wall junction line to lesser curve of the stomach and ensures proper volume of the resultant pouch. The present invention also allows for articulation to ensure proper alignment, ensures EMR (endoscopic mucosal resection), allows for extraction of resected tissue while the device is in place ensuring fasteners hit desired zones and verify EMR. The present invention also allows for the firing of fasteners and approximation of tissue. Ultimately, the present invention allows for verification of EMR and proper line placement, hybrid access, endolumenal access, stomach manipulation and rugae handling and pyloric plugging.

The present invention allows for the preparation of the internal surface of the gastric cavity for the procedures being performed thereon. In particular, and as discussed above in substantial detail, the present invention allows medical practitioners to stretch the stomach in a controlled manner so as to flatten, and draw together, the anterior and posterior cavity walls. This draws the walls together, while also smoothing out the rugae making it easier to perform a hybrid (that is, using both endoscopic and laparoscopic techniques) gastroplasty procedure. The present gastric coil manipulator allows a surgeon to work on the stomach tissue in a predictable manner, which is true even when repeated visits to the treatment site are not required.

The present disclosure presents methods for both laparoscopic and transoral endoscopic usage of the present gastric coil manipulator. As those skilled in the art will certainly appreciate, these different approaches offer different advantages and disadvantages and the approach stylized may be varied to suit the specific needs of the patient.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used system is obtained and if necessary cleaned. The system can then be sterilized. In one sterilization technique, the system is placed in a closed and sealed container, such as a plastic or TYVEK bag. The container and system are then placed in a field of radiation that can penetrate the container, such as gamma radiation, x-rays, or high-energy electrons. The radiation kills bacteria on the system and in the container. The sterilized system can then be stored in the sterile container. The sealed container keeps the system sterile until it is opened in the medical facility.

It is preferred that the device is sterilized. This can be done by any number of ways known to those skilled in the art including beta or gamma radiation, ethylene oxide, and steam.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for stomach manipulation, comprising:
   inserting a medical instrument within a gastric cavity:
   splaying the gastric cavity in a manner eliminating stomach folds and bringing a posterior wall of the stomach into apposition with an anterior wall of the stomach, ensuring proper alignment of the medical instrument and ensuring proper volume of a resultant gastric pouch.

2. The method according to claim 1, wherein the medical instrument includes a gastric coil manipulator including a longitudinally extending shaft having a distal end and a proximal end; a flexible element which extends longitudinally along the shaft and a portion thereof extends beyond the distal end of the shaft for creation of a resilient arc; an actuator cable is secured to the flexible element for manipulation of the portion of the flexible element extending beyond the distal end of the shaft.

3. The method according to claim 2, wherein the shaft is a flexible tubular member.

4. The method according to claim 2, wherein the flexible element is secured to the shaft in a manner allowing for longitudinal movement of the flexible element relative to the shaft.

5. The method according to claim 2, wherein the flexible element includes a first end that is connected to and extends along a length of the shaft and a free second end that extends beyond the distal end, and the actuator cable is secured to the flexible element adjacent the second end of the flexible element for manipulation of the portion of the flexible element extending beyond the distal end of the shaft.

6. The method according to claim 5, wherein the actuator cable includes a second end which is secured to the second end of the flexible element and a first end which is accessible adjacent the proximal end of the shaft for actuation of the flexible element.

7. The method according to claim 2, wherein the actuator cable extends up through a cable support tube mounted adjacent the shaft.

8. The method according to claim 7, wherein the cable support tube is secured to the shaft such that longitudinal axes of the respective cable support tube and the shaft are substantially parallel.

9. The method according to claim 7, wherein the cable support tube is mounted upon the shaft such that the cable support tube may be moved longitudinally relative to the shaft for adjustment of a force vector which the actuator cable applies to the flexible element.

10. The method according to claim 9, further including a handle at the proximal end of the shaft, wherein the handle is further provided with a lever secured to for manipulating position of the cable support tube relative to the shaft.

11. The method according to claim 1, further including the step of fixing the anterior wall and the posterior wall together.

* * * * *